United States Patent
Koblish et al.

(10) Patent No.: US 8,725,228 B2
(45) Date of Patent: May 13, 2014

(54) STEERABLE CATHETER HAVING INTERMEDIATE STIFFNESS TRANSITION ZONE

(75) Inventors: Josef V. Koblish, Sunnyvale, CA (US); Mark Forrest, Sunnyvale, CA (US); Zaya Tun, Livermore, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 654 days.

(21) Appl. No.: 12/708,114

(22) Filed: Feb. 18, 2010

(65) Prior Publication Data

US 2010/0217184 A1 Aug. 26, 2010

Related U.S. Application Data

(60) Provisional application No. 61/154,087, filed on Feb. 20, 2009.

(51) Int. Cl.
*A61B 5/042* (2006.01)
*A61B 18/24* (2006.01)

(52) U.S. Cl.
USPC .............. 600/374; 600/373; 600/509; 606/41

(58) Field of Classification Search
USPC ............. 600/372, 373, 374, 381, 509; 606/41
See application file for complete search history.

(56) References Cited

U.S. PATENT DOCUMENTS 4,739,768 A * 4/1988 Engelson ....................... 600/435
4,921,483 A * 5/1990 Wijay et al. ................... 604/103.1

(Continued)

FOREIGN PATENT DOCUMENTS

| EP | 0842673 | 5/1998 |
|---|---|---|
| EP | 1005838 | 6/2000 |

(Continued)

OTHER PUBLICATIONS

Papers from file history for related U.S. Appl. No. 11/470,132, filed Sep. 5, 2006, Inventor Josef V. Koblish, including (44 pages total): Final Office Action for U.S. Appl. No. 11/470,132, mailed Jan. 15, 2010; Response to Notice of Non-Compliant Amendment to the Office Action dated Jun. 11, 2009 for U.S. Appl. No. 11/470,132, submitted Nov. 2, 2009; Amendment and Response to Office Action dated Jun. 11, 2009 for U.S. Appl. No. 11/470,132, submitted Sep. 9, 2009; Non-Final Office Action for U.S. Appl. No. 11/470,132, mailed Jun. 11, 2009; Amendment and Response to Office Action dated Jan. 9, 2009 for U.S. Appl. No. 11/470,132, submitted Apr. 6, 2009; Non-Final Office Action for U.S. Appl. No. 11/470,132, mailed Jan. 9, 2009.

(Continued)

*Primary Examiner* — Linda Dvorak
*Assistant Examiner* — Erin M Cardinal
(74) *Attorney, Agent, or Firm* — Seager, Tufte & Wickheim, LLC

(57) ABSTRACT

A flexible, steerable intravascular catheter includes an elongate flexible shaft having a heterogeneous or multi-zone stiffness profile or structure. A first or distal portion of the catheter shaft may have a substantially constant or distinct stiffness or flexibility, a second, intermediate or transition section is proximal relative to, and less flexible than, the first section, and a third section is proximal relative to, and also less more flexible than, the first section. The third section also includes a substantially constant or distinct stiffness or flexibility. The flexibility or stiffness of the second section varies along its length, e.g., in a substantially linear, step-like or ramp-like manner to provide a smooth or gradual transition between the stiffness of the first or distal section and the flexibility or stiffness of the third or proximal section.

15 Claims, 12 Drawing Sheets

(56) References Cited

U.S. PATENT DOCUMENTS

| | | | |
|---|---|---|---|
| 4,922,912 A | 5/1990 | Watanabe | |
| 4,940,064 A | 7/1990 | Desai | |
| 5,217,482 A * | 6/1993 | Keith | 606/194 |
| 5,231,995 A | 8/1993 | Desai | |
| 5,254,088 A | 10/1993 | Lundquist et al. | |
| 5,257,451 A | 11/1993 | Edwards et al. | |
| 5,273,535 A | 12/1993 | Edwards et al. | |
| 5,275,162 A | 1/1994 | Edwards et al. | |
| 5,308,342 A * | 5/1994 | Sepetka et al. | 604/525 |
| 5,354,297 A | 10/1994 | Avitall | |
| 5,462,544 A | 10/1995 | Saksena et al. | |
| 5,562,619 A | 10/1996 | Mirarchi et al. | |
| 5,605,543 A * | 2/1997 | Swanson | 604/102.02 |
| 5,651,786 A | 7/1997 | Abela et al. | |
| 5,687,723 A | 11/1997 | Avitall | |
| 5,704,926 A * | 1/1998 | Sutton | 604/526 |
| 5,730,127 A | 3/1998 | Avitall | |
| 5,785,706 A | 7/1998 | Bednarek | |
| 5,824,005 A | 10/1998 | Motamedi et al. | |
| 5,827,278 A | 10/1998 | Webster, Jr. | |
| 5,865,800 A | 2/1999 | Mirarchi et al. | |
| 5,921,924 A | 7/1999 | Avitall | |
| 5,928,191 A | 7/1999 | Houser et al. | |
| 5,964,757 A | 10/1999 | Ponzi | |
| 5,984,907 A | 11/1999 | McGee et al. | |
| 6,002,955 A | 12/1999 | Willems et al. | |
| 6,083,222 A | 7/2000 | Klein et al. | |
| 6,093,177 A * | 7/2000 | Javier et al. | 604/523 |
| 6,141,576 A | 10/2000 | Littmann et al. | |
| 6,144,870 A | 11/2000 | Griffin, III | |
| 6,210,362 B1 | 4/2001 | Ponzi | |
| 6,217,565 B1 * | 4/2001 | Cohen | 604/525 |
| 6,308,090 B1 | 10/2001 | Tu et al. | |
| 6,413,234 B1 | 7/2002 | Thompson et al. | |
| 6,430,426 B2 | 8/2002 | Avitall | |
| 6,485,455 B1 | 11/2002 | Thompson et al. | |
| 6,547,779 B2 * | 4/2003 | Levine et al. | 606/7 |
| 6,716,207 B2 | 4/2004 | Farnholtz | |
| 6,746,446 B1 | 6/2004 | Hill, III et al. | |
| 6,866,662 B2 | 3/2005 | Fuimaono et al. | |
| 6,869,414 B2 | 3/2005 | Simpson et al. | |
| 6,926,669 B1 | 8/2005 | Stewart et al. | |
| 6,987,996 B2 | 1/2006 | Fuimaono et al. | |
| 7,013,170 B2 | 3/2006 | Bowe | |
| 7,081,114 B2 | 7/2006 | Rashidi | |
| 7,089,063 B2 | 8/2006 | Lesh et al. | |
| 7,163,523 B2 * | 1/2007 | Devens et al. | 604/96.01 |
| 7,412,273 B2 | 8/2008 | Jais et al. | |
| 7,419,477 B2 | 9/2008 | Simpson et al. | |
| 7,496,394 B2 | 2/2009 | Ahmed et al. | |
| 7,507,229 B2 * | 3/2009 | Hewitt et al. | 604/527 |
| 2002/0026145 A1 * | 2/2002 | Bagaoisan et al. | 604/96.01 |
| 2002/0177840 A1 | 11/2002 | Farnholtz | |
| 2003/0009095 A1 | 1/2003 | Skarda | |
| 2005/0273006 A1 | 12/2005 | Stewart et al. | |
| 2007/0135733 A1 * | 6/2007 | Soukup et al. | 600/585 |
| 2007/0282358 A1 * | 12/2007 | Remiszewski et al. | 606/159 |
| 2008/0076999 A1 | 3/2008 | Koblish | |

FOREIGN PATENT DOCUMENTS

| | | |
|---|---|---|
| EP | 1502542 | 2/2005 |
| EP | 1532999 | 5/2008 |
| WO | WO 95/10318 | 4/1995 |
| WO | 9640347 A1 | 12/1996 |
| WO | 2006091597 A1 | 8/2006 |

OTHER PUBLICATIONS

PCT International Search Report and Written Opinion for PCT/US2007/077496, Applicant: Boston Scientific Scimed, Inc., Forms PCT/ISA/210, 220, and 237 dated May 7, 2008 (14 pages).

PCT International Preliminary Report on Patentability for PCT/US2007/077496, Applicant: Boston Scientific Scimed, Inc., Forms PCT/IB/326, 373 and PCT/ISA/237 dated Mar. 19, 2009 (9 pages).

Office Action from related EP patent application No. 07814653.7 dated Sep. 10, 2009 (4 pages).

* cited by examiner

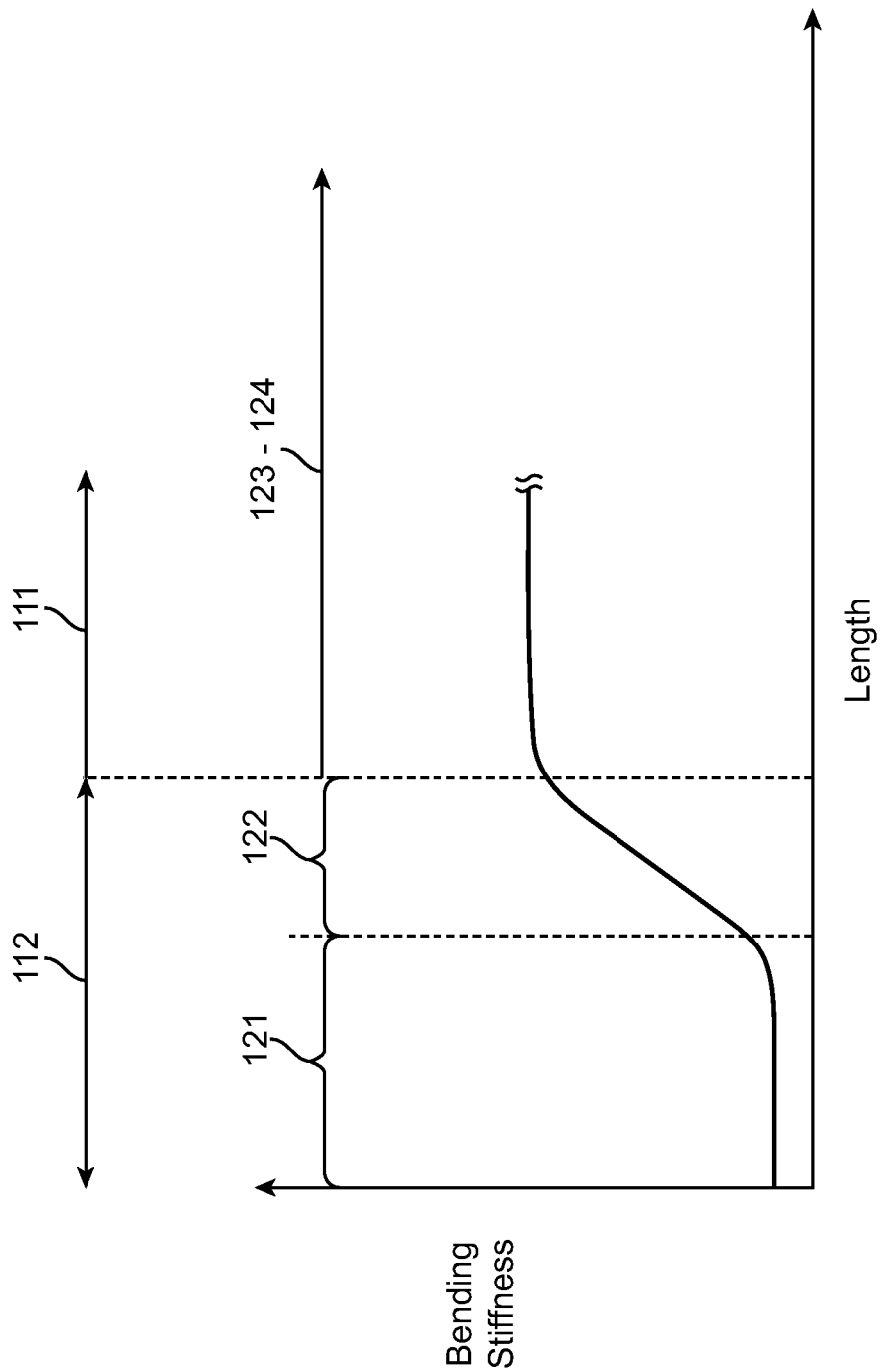

SECTION VIEW

STEERABLE CATHETER HAVING INTERMEDIATE STIFFNESS TRANSITION ZONE

RELATED APPLICATION DATA

The present application claims the benefit under 35 U.S.C. §119 to U.S. provisional patent application Ser. No. 61/154,087 filed Feb. 20, 2009. The foregoing application is hereby incorporated by reference into the present application in its entirety.

FIELD OF INVENTION

The disclosed inventions relate to steerable intra-vascular catheters, such as endovascular electrophysiology mapping and ablation catheters.

BACKGROUND

Electrophysiology is the study of electrical impulses that are transmitted through the heart and is focused primarily on diagnosing and treating arrhythmias, or conditions in which electrical impulses within the heart vary from the normal rate or rhythm of a heartbeat. A common arrhythmia is atrial fibrillation (AF), which is characterized by rapid, disorganized contractions of the heart's upper chambers, the atria. AF results from abnormal electrical impulses propagating through aberrant myocardial tissue pathways, which leads to ineffective pumping of the blood through the heart, as well as other complications. Atria flutter (AFL), another type of arrhythmia, is characterized by a rapid beating of the atria. Unlike AF, AFL arises from a single electrical wave that circulates rapidly throughout the right side of the heart. Since this arrhythmia can arise from multiple electrical sites, effective treatment of these conditions requires electrical isolation of the aberrant signal sites, thereby forcing the heart's normal conduction pathway to take over.

The practice of interventional electrophysiology for treating arrhythmias generally involves inserting catheters into a patient's vasculature (e.g., through the groin and inferior vena cava) and navigating the distal or "working" end of the catheters into the patient's heart chambers to identify or "map" the locations of heart tissue that are a source of the arrhythmias. The mapping of the heart's electrical activity is typically accomplished using one or more pairs of electrodes that are axially spaced apart from each other along the working end of the catheter. Following or in conjunction with the mapping procedure, the attending physician may use a separate ablation catheter or ablation electrode carried by the catheter that is also used for mapping to disable (or "ablate") the tissue containing the aberrant signal(s) or signal pathway(s), thereby restoring the heart to its normal rhythm.

Electrical activity is normally mapped using much smaller electrodes (in surface area) than are used for performing ablation procedures. Because there is significantly less current transmitted through a mapping electrode circuit than through an ablation circuit, lead wires that connect mapping electrodes to processing circuitry (e.g., via a pin connector in the catheter handle) are much smaller than are used to couple ablation electrodes to an RF generator. As such, a larger number of electrodes may be provided on a mapping catheter than on an ablation catheter having a same or similar profile.

Examples and further aspects of known catheters are described in U.S. Pat. Nos. 4,739,768; 5,257,451; 5,273,535; 5,308,342; 5,984,907; and 6,485,455, the contents of which are incorporated herein by reference.

SUMMARY

Embodiments include steerable catheters having a heterogeneous, multi-zone stiffness profile such that a catheter shaft has smooth or gradual transitions between different stiffnesses of distal and proximal portions of the shaft, thereby providing for improved distal torque transmission (ability of the steerable distal portion to transmit input rotational force from the handle to a distal tip), trackability (ability of the entire catheter to follow itself through varying and tortuous anatomy), pushability (ability of the catheter to efficiently move axially through the anatomy), lateral stability (ability of a distal tip electrode to remain stable on the heart tissue when subjected to side loading) and distal durability (ability of the steerable distal portion to remain undamaged when subjected to clinical use). For example, in one embodiment, the shaft is structured such that catheter pushability and torque transmission are maximized, while the most distal portion is structured to emphasize stiffness transition and lateral stability.

In one embodiment, a steerable intravascular catheter comprises an elongate flexible shaft or tube having a proximal portion and a steerable distal portion and that includes a first, distal section, a second, transition section that is proximal relative to, and less flexible than, the first section, and a third section that is proximal relative to, and less flexible than, the first and second sections. The flexibility or stiffness of the second section varies along its length to gradually transition between the first and third sections. The steering apparatus can be integrated into various shafts of various catheters.

In another embodiment, a steerable intravascular catheter comprises an elongate flexible shaft or tube having a proximal portion and a steerable distal portion. The shaft includes a first, distal section, a second, transition section that is proximal relative to, and stiffer or less flexible than, the first section, and a third section that is proximal relative to, and stiffer or less flexible than, the first and second sections, and a fourth section that is proximal relative to the third section and stiffer or less flexible than the first, second and third sections. The flexibility or stiffness of the first section is substantially constant along its length, and the flexibility or stiffness of the second section varies along its length to gradually transition between the first section and the third section. The steering apparatus can be incorporated into a shaft of various catheters.

According to a further embodiment, a steerable intravascular catheter comprises an elongate, flexible shaft, a steering apparatus and an electrode. The shaft has a proximal portion, which may extend from a handle, and a steerable distal portion. The electrode is carried on the steerable distal portion of the shaft. The steering apparatus is positioned within the shaft and includes a first, distal section, a second, transition section that is proximal relative to and stiffer or less flexible than, the first section, and a third section that is proximal relative to, and stiffer or less flexible than, the first section. The flexibility or stiffness of the second section varies along its length to transition between the first and third sections. The catheter shaft may also include one or more control elements or wires that can be manipulated to move the steering apparatus and catheter shaft in different directions.

In one or more embodiments, the stiffness of the catheter shaft is varied along the length to provide a gradual transition by incorporating various stiffness zones directly into an outer tubing of the catheter shaft or body. For example, tubing segments of various stiffnesses may be stacked on a common inner core and thermally fused into a single shaft. In this manner, the resulting shaft has at least two distinct stiffness zones and a "transition zone" or "step-like" or "ramp-like" transition between the two stiffness zones. In another embodiment, extrusion technologies such as interrupted co-extrusion may be used that directly integrate materials of different stiffnesses into a single tube over a common lumen. The resulting tube will have at least two distinct stiffness zones and a transition zone between the two stiffness zones.

In one or more embodiments, a gradual transition between two adjacent stiffness zones of a distal portion of a shaft is may be substantially linear, e.g., as a step-like or ramp-like transition or slope between two stiffness levels. The gradual transition may also be non-linear, e.g., parabolic or exponential. The first or distal section may also transmit less torque than the second section, which may transmit less torque than the third section.

In one or more embodiments, a catheter may include one or more additional sections. For example, a fourth section may be proximal relative to the third section and stiffer or less flexible than each of the more distal sections. The fourth section may have a substantially constant or distinct stiffness or flexibility.

In one or more embodiments, at least one other section of a catheter steering apparatus other than an intermediate or second section includes a variable flexibility or stiffness along at least a portion of its length. For example, the flexibility or stiffness of at least a portion of the third section can vary along its length. In this embodiment, the third section may include multiple segments. A first segment of the third section is proximal relative to and adjacent to the second section. A second segment of the third section is proximal relative to and adjacent to the first segment of the third section and is stiffer or less flexible than the first segment of the third section. The first or distal section of the steering apparatus has a substantially constant or distinct flexibility or stiffness along its length, and the flexibility or stiffness of the second segment of the third section also varies along its length. The rate at which the stiffness or flexibility changes in the second section is more gradual than the rate which stiffness or flexibility changes in the second segment of the third section.

In one or more embodiments, the first or distal section of a catheter shaft includes a substantially constant or distinct flexibility or stiffness along its length. At least a portion of the third section is stiffer than the first section and has a substantially constant or distinct flexibility or stiffness.

In one or more embodiments, the first or distal section of a catheter shaft includes an internal support member, which may be formed from or made of a material that has a yield strength greater than about 120,000 pounds per square inch (psi). In one embodiment, the internal support member has a yield strength of about 140,000 psi and may be Type 301 stainless steel.

Other and further aspects and embodiments of the disclosed inventions are described in the detailed description of the accompanying drawings.

BRIEF DESCRIPTION OF THE DRAWINGS

It will be appreciated that the embodiments and components thereof shown in the drawings are not necessarily drawn to scale, with emphasis instead being placed on illustrating the various aspects and features of the illustrated embodiments, in which:

FIG. 5A is a graph generally illustrating stiffness attributes of different sections of a catheter constructed according to one embodiment and having a step-like or ramp-like stiffness profile;

DETAILED DESCRIPTION OF ILLUSTRATED EMBODIMENTS

Figure 1:
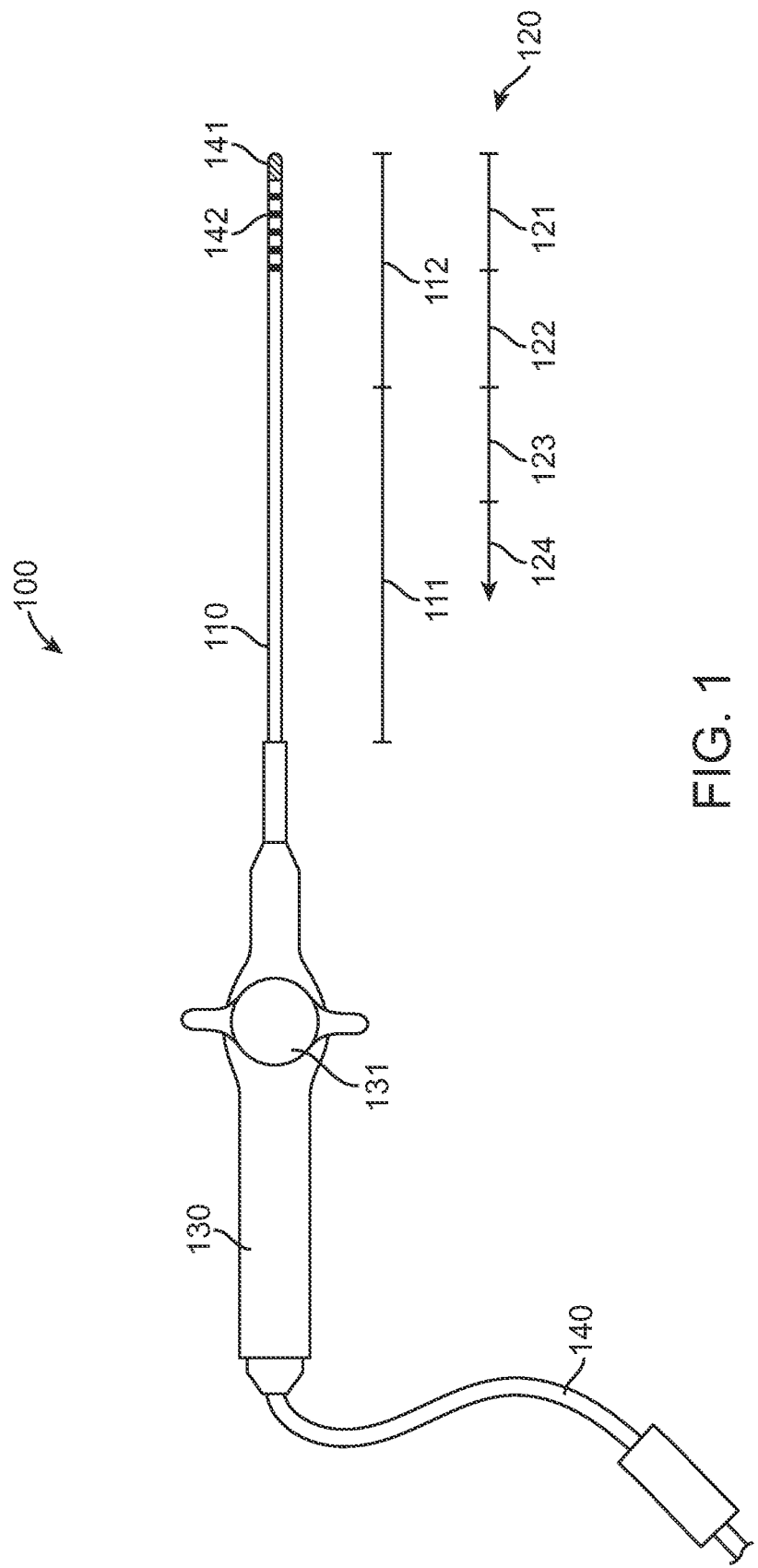
FIG. 1 illustrates a catheter constructed according to one embodiment that includes a multi-zone structure having sections of different stiffness or flexibility.

Referring to FIG. 1, a bi-directional steerable catheter 100 constructed according to certain embodiments includes an elongate, flexible shaft 110 that is structurally configured to have a heterogeneous, multi-zone stiffness profile or structure 120 having different or variable rigidity, stiffness or flexibility along its length. For ease of explanation, this specification generally refers to a multi-zone structure or profile 120 having different stiffness attributes, noting that sections having different stiffnesses have different flexibilities.

As shown in FIG. 1, the shaft 110 extends from a distal portion of a handle 130, as is known in the art of electrophysiology catheters. The catheter shaft 110 generally includes a proximal section or portion 111 and a steerable distal section or portion 112 that is sized and configured for placement and manipulation within in a heart of patient without prolapsing. FIG. 1 generally illustrates proximal and distal portions 111, 112, but the lengths of these portions 111, 112 and the dividing line between these portions 111, 112 may vary in different implementations and catheter designs. An electrical cable or other suitable connector 140 extending from a proximal end of the handle 130 may be coupled to a source of energy or other equipment (not shown in FIG. 1) for transmitting one or more ablation signals and/or receiving signals or data from mapping electrodes. FIG. 1 generally illustrates electrodes as a distal tip electrode 141 and shaft or ring electrodes 142.

Figure 2:
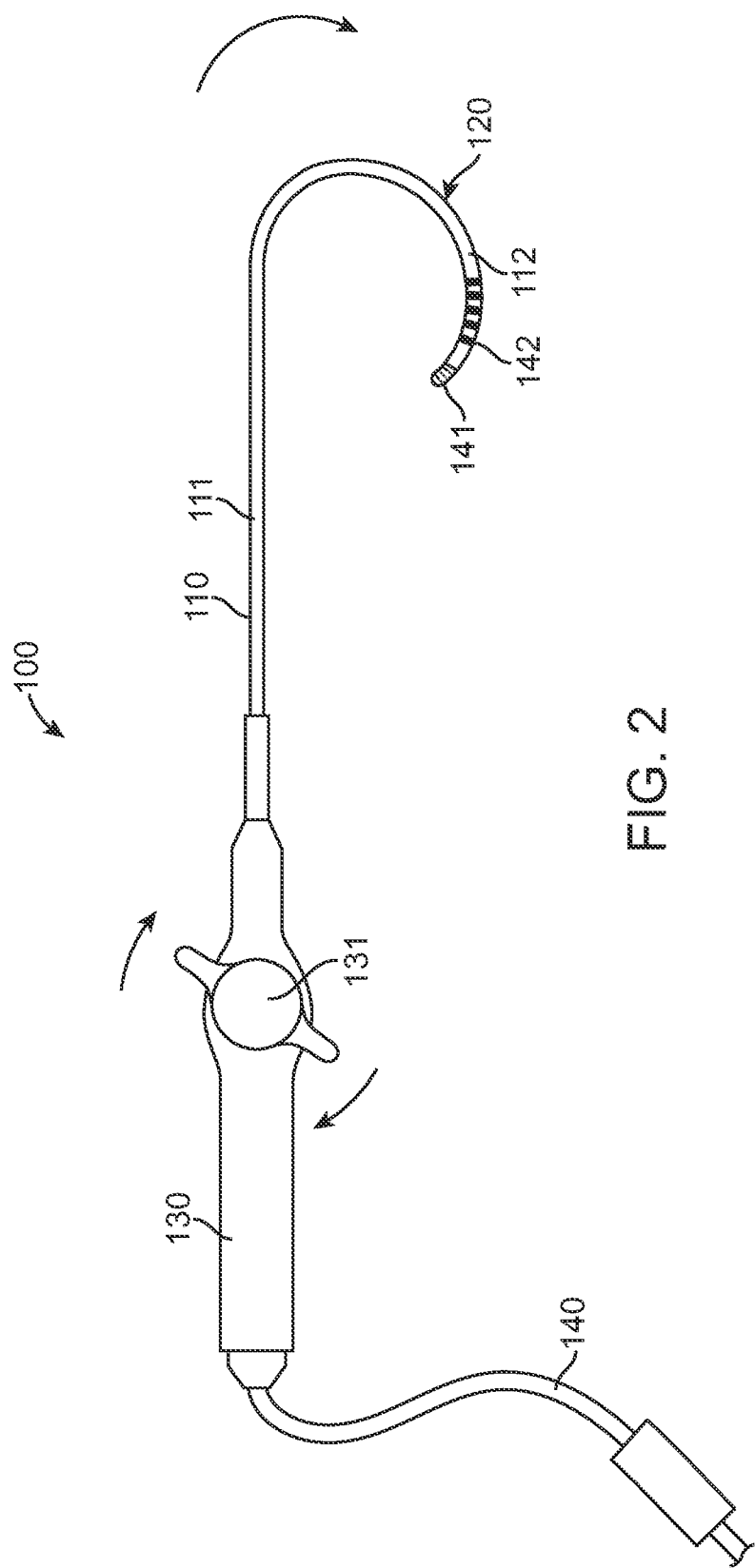
FIG. 2 illustrates bending of the catheter shown in FIG. 1 in a first direction.
Figure 3:
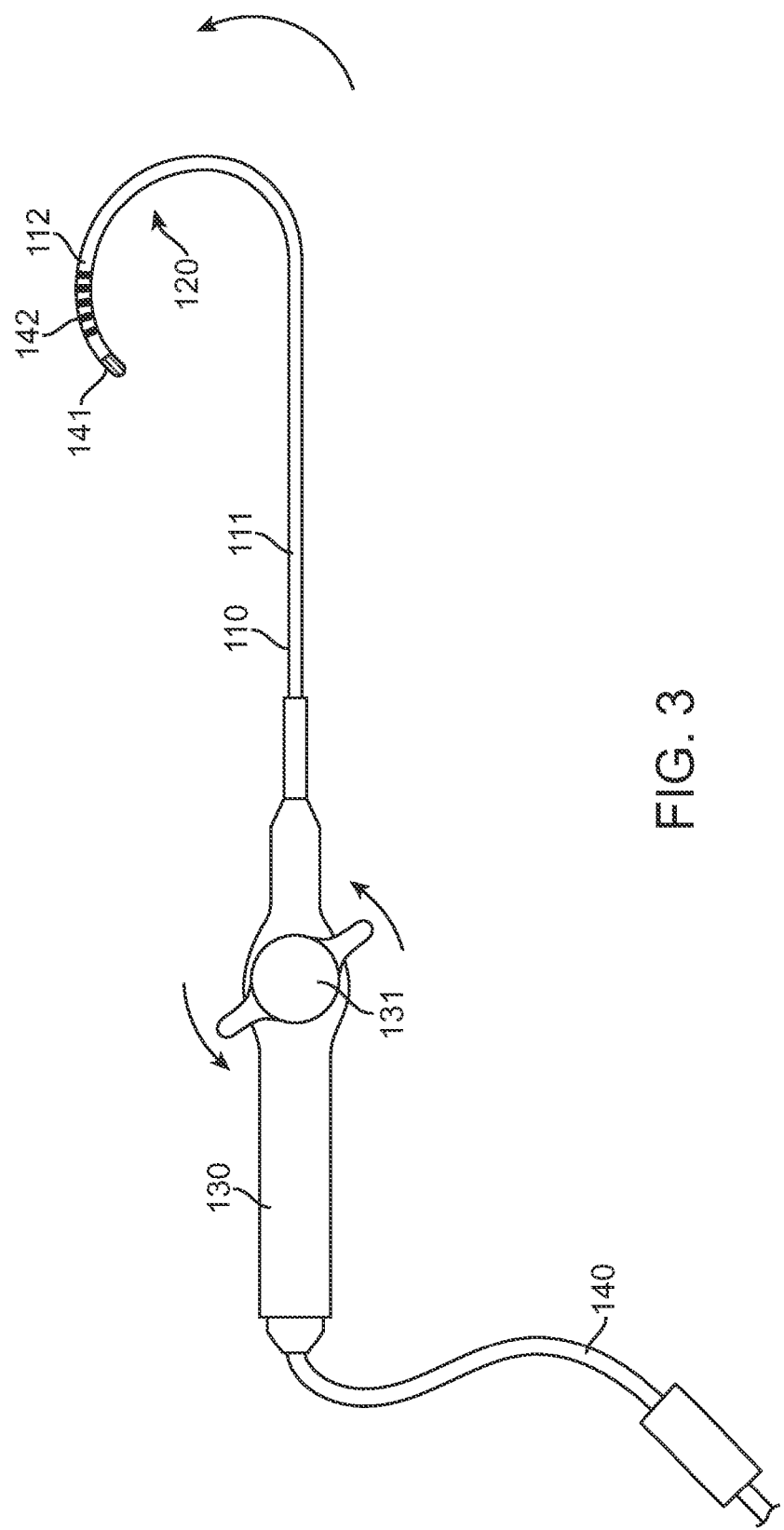
FIG. 3 illustrates bending of the catheter shown in FIG. 1 in a second direction.
Figure 4:
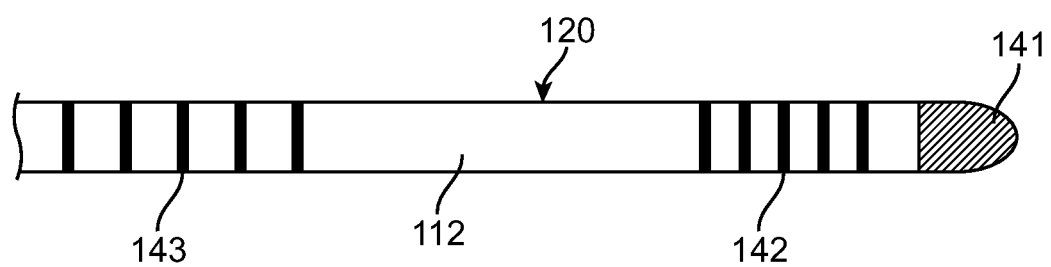
FIG. 4 illustrates a distal bending portion of a catheter and mapping and ablation electrodes.

With further reference to FIGS. 2-3, during use, the catheter shaft 110 is advanced into a patient, e.g., through a puncture into the femoral vein of a patient, through the inferior vena cava and into the right atrium using a bi-directional steering support member 610 (shown in FIG. 6A) that is embedded in the distal portion 112. An actuator 131, such as a rotatable knob or dial as shown in FIG. 2, can be manipulated by the surgeon to position the distal section 112 of the shaft 110 as desired by adjusting tension on the steering member, e.g., forming the distal section 112 into a three-quarter loop in different directions as shown in FIGS. 2-3. After the catheter's distal section 112 is properly positioned, an electrical current can be applied to one or more electrodes through the connector or cable 140 to map and/or ablate target tissue. For example, non-ablative energy can be applied to target tissue through one or more mapping electrodes 142, and ablation energy can be applied to target tissue through a distal tip ablation electrode 141. While FIGS. 1-3 illustrate one manner in which electrodes 141, 142 may be configured, other electrode configurations may be utilized. For example, FIG. 4 shows ring electrodes 142, 143, and an ablation tip electrode 141. Thus, various electrode configurations may also be utilized, and the electrodes may be used for ablation and/or mapping.

In the embodiment illustrated in FIG. 1, and with further reference to FIG. 5A (illustrating a distal-to-proximal bending stiffness profile of a catheter 100 constructed according to one embodiment), the shaft 110 includes, or is formed or designed to have, a heterogeneous, multi-zone structure or profile 120 that includes different stiffness zones. The embodiment of a stiffness profile illustrated in FIG. 5A includes four different stiffness zones 121-124, but other embodiments may include different numbers of stiffness zones, e.g., three, five or other numbers of stiffness zones. In the illustrated embodiment, zones 121 and 122 form a distal section 112 of the shaft, and zones 123 and 124 form a proximal portion 111 of the shaft 110. At least one stiffness zone, e.g., zone 122 of the distal portion 111 in the illustrated embodiment, is an intermediate stiffness zone that is configured to provide a smooth, gradual transition, step or ramp between two other zones 121 and 123 having different stiffness attributes.

Different zones 121-124 may have different stiffness attributes as a result of having different stiffness magnitudes, i.e., one zone is stiffer or more flexible than another, different stiffness profiles or patterns, i.e., a zone may have a constant or substantially constant (i.e., distinct) stiffness, a variable stiffness, or both. Different zones of the multi-zone structure 120 can be formed or fabricated in different ways. In one embodiment, the stiffness of the catheter shaft 110 is varied along the length by incorporating various stiffness zones directly into an outer tubing of the catheter shaft 110 or body. For example, sections of tubing with varying stiffness may be stacked on a common inner core and thermally fused into a single shaft 110. In this manner, the resulting shaft 110 has at least two distinct stiffness zones and one transition zone there between. In another embodiment, extrusion technologies such as interrupted co-extrusion may be used to directly integrate varying stiffness materials into a single tube over a common lumen. The resulting tube(s) will have at least two distinct stiffness zones and at least one intermediate transition zone between two stiffness zones. Each of the zones 121-124 can be same length or different lengths. It should be understood that a multi-zone structure 120 can be constructed in other ways, e.g., by selection and configuration of certain internal materials and components, and that these configurations and methods of fabrication are provided as examples of how embodiments may be implemented to provide for more gradual transitions between different sections of the catheter shaft 110, thereby providing improved pushability, tracking, and torsional strength and a smoother transition of flexibility along the length of the shaft 110 to optimize each section of the shaft 110. For ease of explanation, this specification refers to different materials and material configurations that can be used to implement a particular zone, but it should be understood that a multi-zone structure 120, including the multi-zone structure 120 illustrated in FIG. 5A, can be implemented in other ways.

Figure 5B:
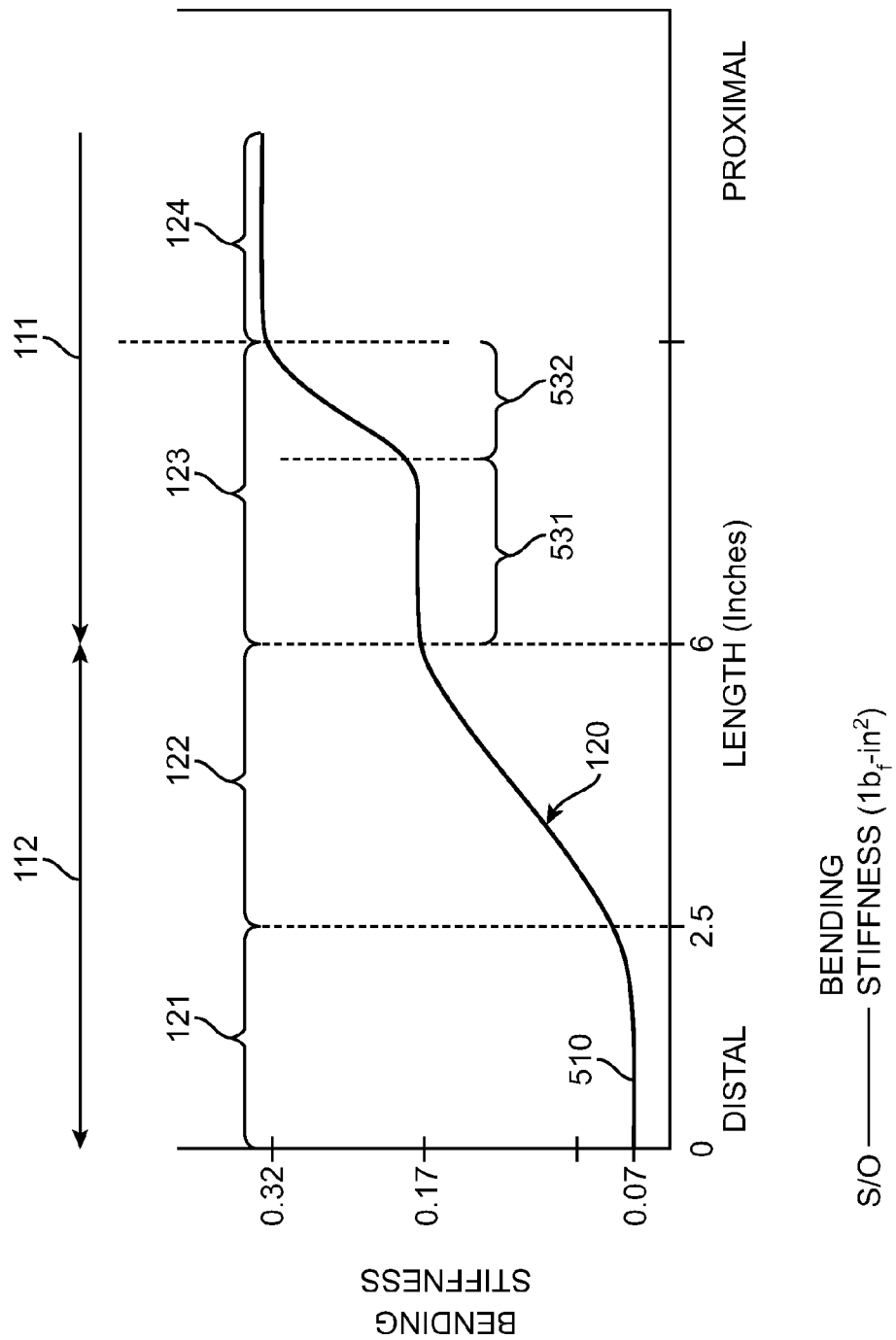
FIG. 5B is a graph illustrating bending stiffness attributes of different sections of a catheter constructed according to one embodiment and having a multi-zone stiffness structure.
Figure 6:
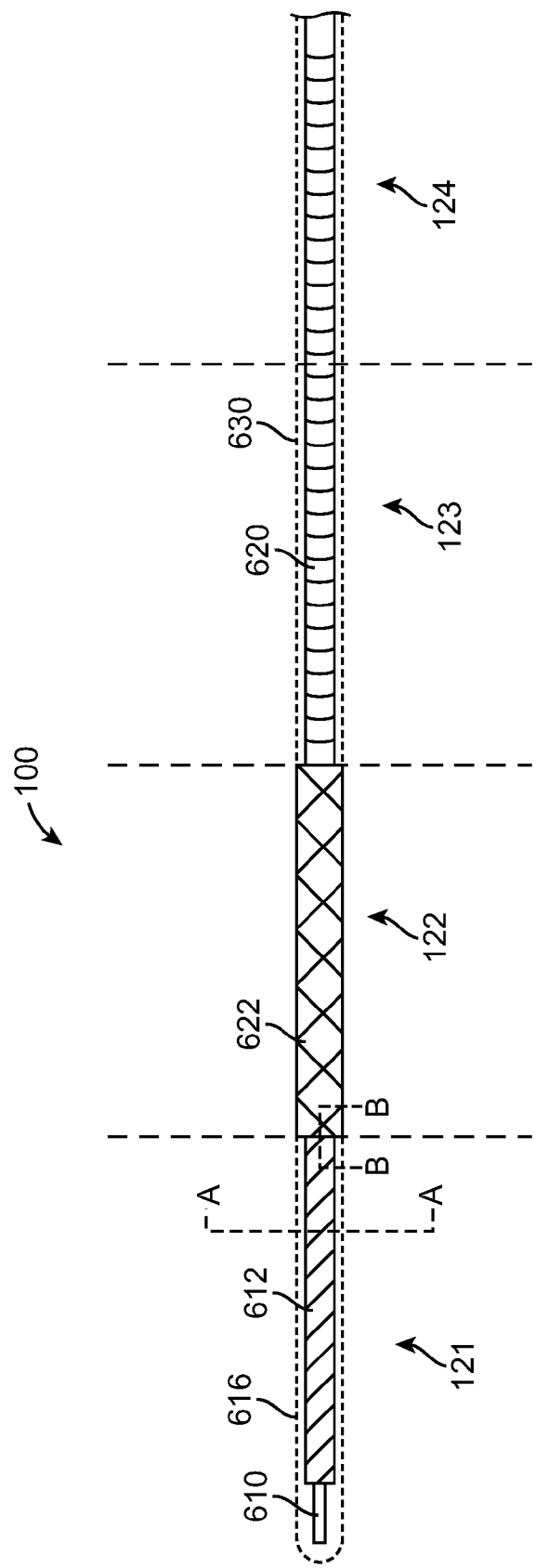
FIG. 6 illustrates different components or layers of a catheter that may be constructed to have stiffness profiles as shown in FIGS. 5A-B.

With further reference to FIGS. 5B and 6, in one embodiment, the catheter shaft 110 is structured to include four different stiffness zones 121-124. FIG. 5B illustrates stiffness in terms of lbf-in2, how bending stiffness varies across a length of a catheter shaft 110 constructed according to one embodiment, and how the bending stiffness of the intermediate or transition portion 122 varies according to embodiments. In the embodiment illustrated in FIG. 5B, the bending stiffness 510 increases across four zones 121-124 from the distal portion 112 (left edge of the graph shown in FIG. 5) to the proximal portion 111 (right edge of the graph shown in FIG. 5B) of the catheter shaft 110.

In one embodiment, as shown in FIG. 5B, a catheter shaft 110 can have a length of about 35-45 inches, and the first or distal zone 121 of the distal portion 111 of the shaft 110 can have a length of about 1.5 inches to about 4.5 inches, e.g., about 2.5 inches, a diameter of about 0.092 inches (and other suitable diameters), and be made of or include a polyether-polyamide block copolymer and Type 301 stainless steel (and other suitable materials). The second zone 122 of the distal portion 111 of the shaft 110 can have a length of about 1.0 inch to about 4.0 inches, e.g., about 1.75 inches, a diameter of about 0.092 inches (and other suitable diameters) and be made of or include a polyether-polyamide block copolymer and Type 301 stainless steel (and other suitable materials). Thus, in the illustrated embodiment, the distal portion 112 of the shaft 110 includes the intermediate or stiffness transition zone and can have a length of about 6 to about 9 inches, e.g., about 7 inches.

In the embodiment illustrated in FIG. 5B, the third zone 123, which can be a part of the proximal portion 112 of the shaft 110, can have a length of about 1 to 4 inches and a diameter of about 0.092 inch (or other suitable diameters) and be made of or include a polyether-polyamide block copolymer and Type 301 stainless steel (and other suitable materials). The fourth zone 124, which is also part of the proximal portion 112 extends to the handle 130 and can have various lengths, e.g., about 25.5 inches to about 36.0 inches and may have a diameter of about 0.092 inches (or other suitable diameter) and be made of or include a polyether-polyamide block copolymer and Type 301 stainless steel (or other suitable materials).

Different zones 121-124 can be defined by sections having different diameters and including or being made of different materials. Thus, the dimensions, ranges of dimensions, and materials mentioned above are provided as examples of how embodiments may be implemented, and stiffness profiles according to embodiments can be implemented using components and structures that are described in U.S. Pat. No. 5,984,907, the contents of which were previously incorporated herein by reference as though set forth in full.

With a shaft 110 configured as in the embodiment illustrated in FIGS. 5B and 6, the bending stiffness 510 of the first zone 121 of the distal portion 111 is distinct (constant or substantially constant) across its length, e.g., about 0.01 lbf-in2 to about 0.1 lbf-in2, e.g., about 0.07 lbf-in2 along its length, which may be about 2.5". As shown in FIG. 5B, the stiffness of the proximal end of the first zone 121 may begin to step or ramp up and increase slightly at or near the proximal end of the first zone 121 or at or near the distal end of the second zone 122, depending on the type of transition that is utilized in the second zone 122.

In the embodiment illustrated in FIG. 5B, the second zone 122 of the distal portion 112, which is proximal relative to and adjacent to the first or distal zone 121, is an intermediate transition zone located between the first zone 121 of the distal portion 112 and the third zone 123, which is shown as being a part of the proximal portion 111 of the shaft 110. The second zone 122 has a bending stiffness 510 that varies across its length. In other words, the bending stiffness profile of the second zone 122 is not distinct or substantially constant along its length as in the first zone 121 and/or the third zone 123 or other, more proximal zones. In one embodiment, the stiffness varies in a substantially linear manner and may do so in a step-like or ramp-like manner.

In the embodiment illustrated in FIG. 5B, the bending stiffness varies substantially linearly in a step-like or ramp-like manner from about 0.01 lbf-in2 to about 0.10 lbf-in2, e.g., 0.07 lbf-in2, to up to about 0.2 lbf-in2, e.g., up to about 0.17 lbf-in2 over a length of about 1.5" to about 4", e.g., about 2.5". Thus, in one embodiment, the intermediate or transition zone 122 has a bending stiffness that varies by about 0.04 lbf-in2 per inch of length. For this purpose, the second zone 122 may include or be composed of a polyether-polyamide block copolymer and Type 301 stainless steel and have a diameter of about 0.092 inches.

Although FIG. 5B illustrates an intermediate transition zone 122 including a substantially linear step-like or ramp-like stiffness profile, in other embodiments, the stiffness profile of the transition zone 122 may vary in a non-linear manner, e.g., in a curved or exponential manner. Thus, FIG. 5B is provided to illustrate one example of how embodiments can be implemented.

In one embodiment, the bending stiffness 510 of the third zone 123, which can be a part of the proximal portion 111 and is proximal relative to the first and second zones 121, 122 of the distal portion 112, is distinct (constant or substantially constant) along its length. According to one embodiment, the bending stiffness of the third zone 123 is about 0.17 lbf-in2. In this manner, the third zone 123 may be structured in a manner that is similar to the first zone 121 of the distal portion 111 except that the third zone 123 is stiffer or less flexible than the first zone 121.

In another embodiment, the third zone 123 includes multiple sub-zones or segments. For example, as shown in FIG. 5B, the third zone 123 includes a first sub-zone or segment 531 and a second sub-zone or segment 532. The length of the first segment 531 can be about 0.5" to about 2", and the length of the second segment 532 can also be about 0.5" to about 2". In the illustrated embodiment, the first segment 532 has a distinct (constant or substantially constant) stiffness 510 of about 0.17 lbf-in2, and the second sub-zone or segment 532 has a stiffness 510 that varies in a step-like or ramp-like manner across its length from about 0.17 lbf-in2 up to about 0.5 lbf-in2, e.g., about 0.32 lbf-in2. In the illustrated embodiment, the bending stiffness across the second segment 532 varies in a substantially linearly manner. Thus, in the illustrated embodiment, the third zone 123 is a "combination" transition zone that includes multiple transition zones and at least one segment 531 (other than the transition zone 120) that has a distinct stiffness and another segment 532 that provides a transition or stiffness that varies along its length. This type of stiffness profile of the first, second and third zones 121-123 as illustrated in FIG. 5B enhances trackability of a catheter 100 through a tortuous vasculature.

In the illustrated embodiment, the rate at which the stiffness 510 changes in the second zone 122 is less than the rate at which the stiffness 510 changes in the second segment 532 of the third zone 123. In one embodiment, the rate at which stiffness 510 changes in the second zone 122 is about 0.04 lbf-in2 per inch, and the rate at which stiffness 510 changes in the second segment 532 of the third zone 123 is about 0.1 lbf-in2 per inch. In other embodiments, the rate at the stiffness 510 varies in the second zone 122 may be greater than or the same as, the rate at which the stiffness 510 varies in a segment of the third zone 123.

In the illustrated embodiment, the stiffness 510 of the fourth zone 124, which is proximal relative to the first, second and third zones 121-123, also has a distinct (constant or substantially constant) stiffness across its length, similar to the stiffness profile of the first zone 121 and the third zone 123 (or segment 531 thereof). In one embodiment, as illustrated in FIG. 5B, the stiffness 510 of the fourth zone 124 is substantially constant and is about 0.32 lbf-in2 over a length to the handle 130.

Thus, in the illustrated embodiment, the particular stiffness values of each zone 121-124, and the manner in which the stiffness profiles of respective zones 121-124 are substantially constant or vary across a length of a zone, result in an intermediate or transition section or zone 122 that is stiffer or less flexible than the most distal or first section or zone 121, and more flexible than the proximal portion 111, which includes zones 123 and 124. With this particular structural configuration, embodiments provide for a more gradual transition between two distinct stiffness zones (or a segment thereof) and enhance pushability, tracking, and the torsional strength or rigidity of the catheter 100.

Figure 6A:
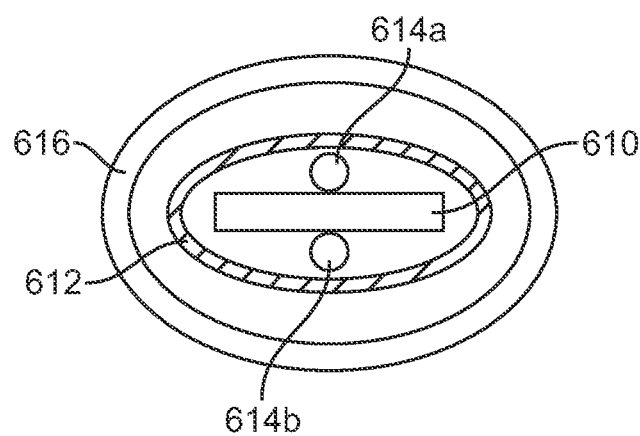
FIG. 6A is a cross-sectional view of FIG. 6 along line A-A.
Figure 6B:
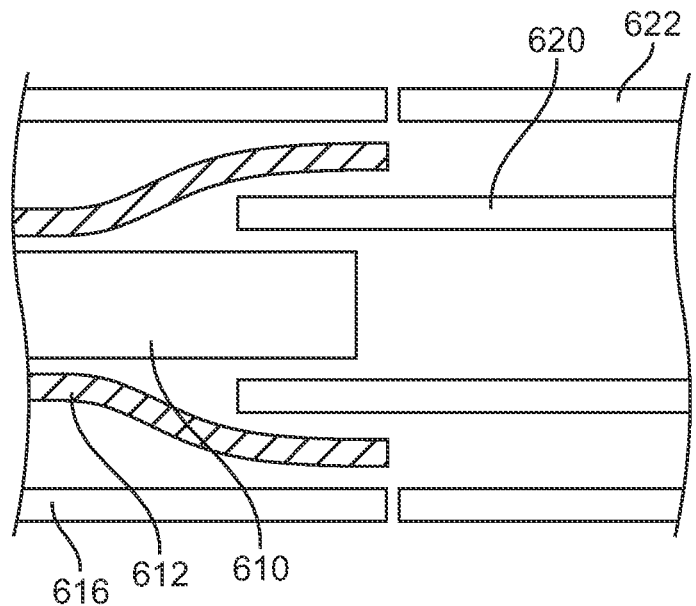
FIG. 6B is a cross-sectional view of FIG. 6 along line B-B.
Figure 7:
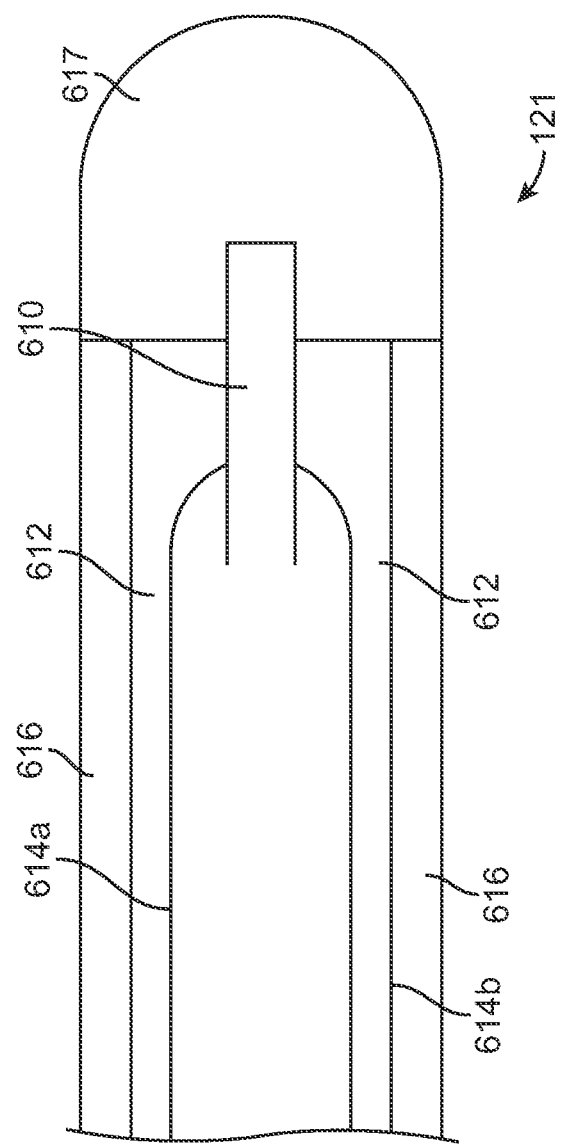
FIG. 7 is a partial cross-sectional view of a distal portion of the catheter shown in FIGS. 6 and 6A.

Referring again to FIG. 6, and with further reference to FIGS. 6A-B and 7, the distal or first zone or section 121 of a catheter shaft 110 includes a center support member 610 that is encased in a reinforcing sleeve 612. The center support member 610 terminates in a rounded tip 617 and is embedded within and connected to the tip 617 by solder or another suitable connection. As shown in FIG. 6A, the sleeve 612 maintains steering wires 614a,b (generally 614) in position against the center support member 610 in order to prevent kinking or tangling of the steering wires 614. The first zone 121 also includes tubing 616 that surrounds the sleeve 612 and the center support 610, as shown in phantom in FIG. 6. The first zone 121 may optionally include leaf springs that are attached to the center support 610.

In one embodiment, the material of the center support 610 is a high yield strength material having a yield strength that is greater than about 120,000 psi. In one embodiment, the internal support member has a yield strength of about 140,000 psi and may be made of Type 301 stainless steel. Such material attributes advantageously provide increased lateral rigidity and greater resistance to permanent deformation of the distal portion 112 of the catheter shaft 110. In other embodiments, the material of the center support 610 may be Type 17-7 PH stainless steel, which has a yield strength of 185,000 psi, Type 440C stainless steel, which has a yield strength of 275,000 psi, and other suitable high yield strength materials.

Figure 8:
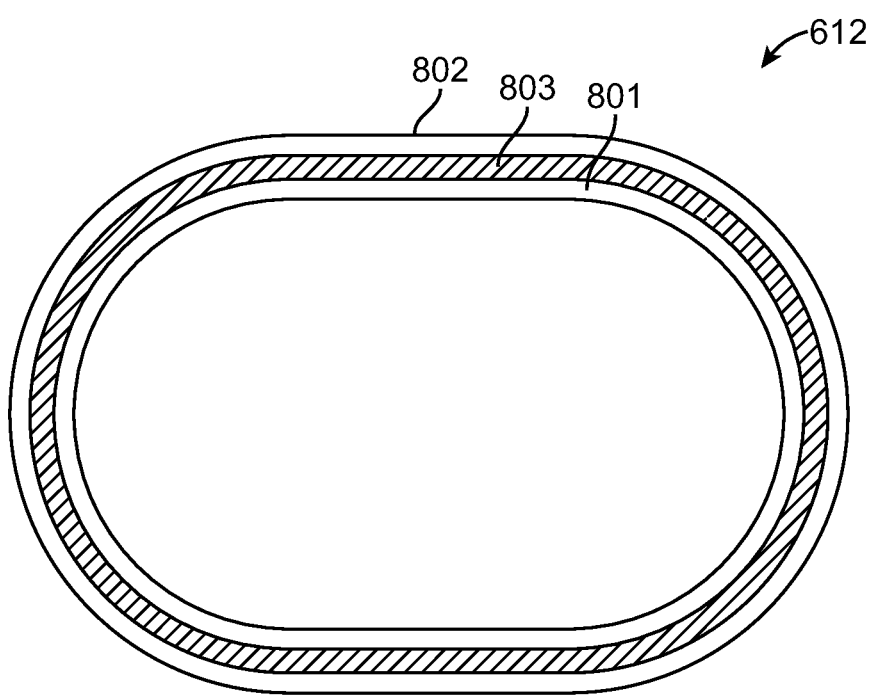
FIG. 8 is a cross-sectional view of a multi-layer reinforcing sleeve constructed according to one embodiment.

Referring to FIG. 8, the reinforcing sleeve 612 encasing the center support 610 may, for example, be made from an inner shrink tube 801, an outer shrink tube 802, and a reinforcing fabric 803 there between. The inner and outer tubes 801, 802 may be made of Teflon® polytetrafluoroethylene and the fabric 803 may be a Kevlar® polyaramid material, e.g., in the form of a yarn, which is wrapped in tension over the inner shrink tube 801 as a single spiral about the tube 801 in order to obtain a desired, closely spaced pitch, and the outer shrink tube 802 may be positioned over the reinforcing fabric 803.

Figure 8A:
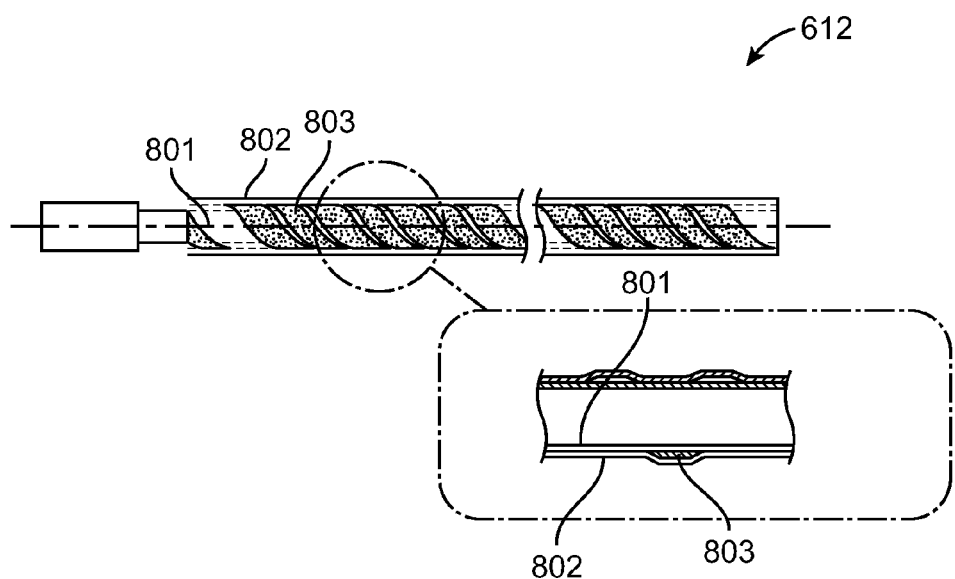
FIG. 8A is a side view of a reinforcing sleeve constructed according to one embodiment that includes a tube having a fabric material wound around an inner tube to a pitch of about 30-35 wraps per inch.
Figure 8B:
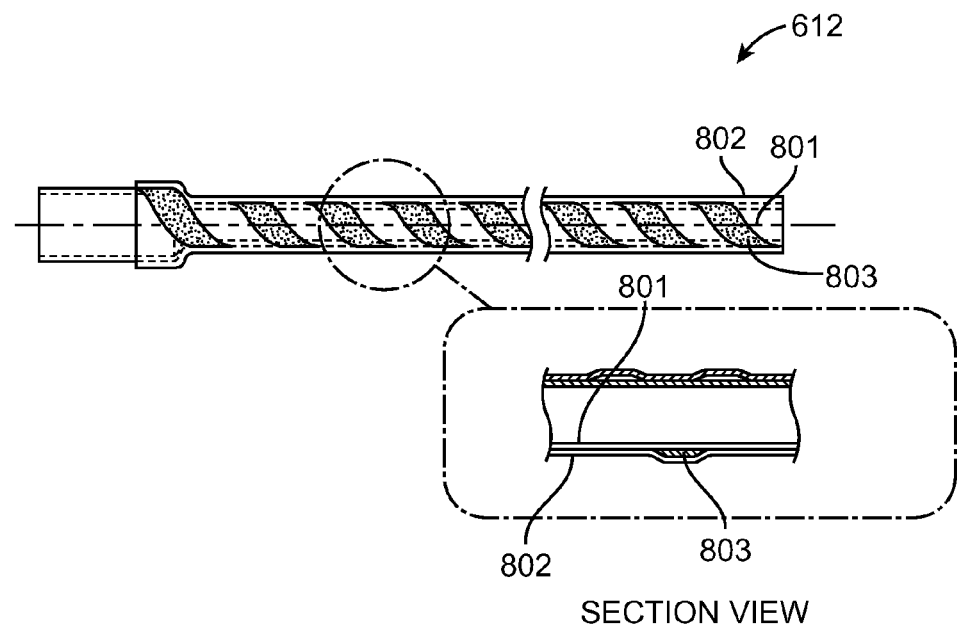
FIG. 8B is a side view of a reinforcing sleeve constructed according to one embodiment that includes a tube having a fabric material wound around an inner tube to a pitch of about 15-20 wraps per inch.

For example, the fabric 803 can be wrapped around the tube 801 to a pitch of about 30 to 35 wraps per inch (e.g., as shown in FIG. 8A). Alternatively, the pitch may be 15 to 20 wraps per inch (e.g., as shown in FIG. 8B). If necessary, a first shrink step may be performed on the inner shrink tube 801 before the reinforcing fabric 803 is applied thereto, and a second shrink step may be performed on the second shrink tube 802 after the second shrink tube 802 is positioned over the reinforcing fabric. 803. The configuration of the sleeve 612 may vary as necessary and depending on the manufacturing method and braid density employed. Thus, the cross-sectional view of a sleeve 612 may be as shown in FIG. 8, in which the fabric or braiding 803 extends around the inner tube 801, or the layer 803 may be less dense, e.g., as shown by the braiding pattern employed in FIG. 8B.

Figure 9:
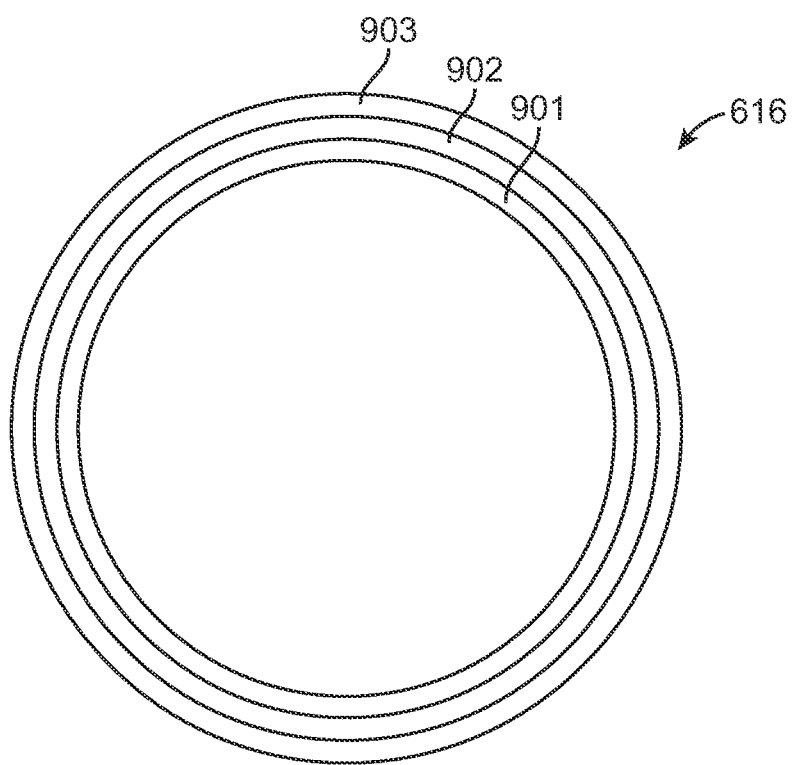
FIG. 9 is a cross-sectional view of distal tubing constructed according to one embodiment.

The tubing 616 may be composite tubing comprised of a fiber-reinforced dual polymer layer. The tubing 616 material may depend on the desired bending stiffness and torsional rigidity in the first zone 121. For example, with reference to FIG. 9, stiffer, distal tubing 616, having a higher torsional rigidity, may include an inner layer 901 of 63D Pebax® fiber, a Vectran® liquid crystal polymer reinforcing braid 902, and a 40D outer layer 903, while softer, composite tubing, having a lower torsional rigidity, may include an inner layer 901 of 55D Pebax®, a Vectran® liquid crystal polymer reinforcing braid 902, and a 35D outer layer 903. The reinforcing fabric braid 902 may add torsional rigidity to the first zone 121 without the risk of the electrical shorting that a metallic braid would impart. The increased torsional strength provided by the braid 902 may help to prevent wind-up of the distal section 112 of the catheter 100 when the handle 130 and/or proximal portion 111 of the catheter 100 are rotated. The fabric braid 902 may also add to the lateral or side load strength of the steered distal portion 112 because the braid 902 adds to the torsional strength of the tubing 616.

Referring again to FIGS. 6A-B, in the illustrated embodiment, the proximal ends of the center support 610 and the reinforcing sleeve 612 are coupled to a flexible inner shaft 620 at the junction between the distal or first zone 121 and the transition or second zone 122. The flexible inner shaft 620 may extend from the center support 610 to a handle assembly 130 on the proximal end of the catheter 100 and may comprise a stainless steel coil. The proximal end of the center support 610 may fit within the distal end of the inner shaft 620, and the proximal end of the reinforcing sleeve 612 may fit over the distal end of the inner shaft 620, thereby providing a smoother transition between the center support 610 and the coil inner shaft 620.

In the second or transition zone 122, the flexible inner shaft or tubing 620 may be enclosed by a stiffening sheath 622, while in the third zone 123 and the fourth zone 124, the flexible inner shaft 620 may be enclosed by a main sheath or tubing 630 (shown in phantom in FIG. 6). The mechanical properties of the stiffening sheath 622 are such that the stiffness of the second zone 122 is between the stiffness of the first zone 121 and the stiffness of the third zone 123, thus advantageously providing a gradual transition between the first zone 121 and the third zone 123 over the length of the second or transition zone 122. The gradual transition achieved with embodiments over a length of the second zone 122 improves the trackability of the catheter 100. For this purpose, the second zone may be comprised of a stiffening sheath 622.

In the third and fourth zones 123 and 124, respectively, the inner shaft 620 is covered by the main sheath 630. While the third zone 123 is stiffer than the first and second zones 121, 122, the third zone 123 should be sufficiently compliant or flexible to bend freely as the catheter 100 tracks through the anatomy (e.g., an aortic arch), yet sufficiently stiff or rigid to be highly pushable. For this purpose, a main sheath 630 may surround the inner shaft 620, and the main sheath 630 may be comprised of a braided material.

The fourth zone 124 comprises the proximal portion of the main sheath 630 (which may also form a part of the third zone 123 as shown in FIG. 6) and may have increased stiffness compared to the third zone 123. The added stiffness of the fourth zone 124 may be accomplished by inserting a stiff metallic rod (not shown) within the catheter shaft 110. For example, a long steel wire may be inserted into the proximal shaft for increased rigidity. Such a wire may be positioned within a lumen of the inner shaft 620 or between an outer surface of the inner shaft 620 and an inner surface of the main sheath 630. The resulting enhanced stiffness of the fourth zone 124 may provide increased pushability, torque, and steering fidelity of the catheter shaft 110.

Further aspects of certain components and examples of components that may be utilized to implement embodiments are described in further detail in U.S. Pat. No. 5,984,907, the contents of which were previously incorporated herein by reference as though set forth in full.

It will be apparent to those skilled in the art that the invention may be embodied in other specific forms besides and beyond those described herein. For example, a multi-zone structure 120 may have different numbers of zones and different zone profiles, while still having an intermediate or transition zone to provide a smooth or gradual transition between distal and more proximal portions of a shaft. Further, different stiffness zones can be formed in various ways, e.g., by adding layers around a catheter, or forming a catheter section of a different material, and/or integrating different internal materials such as an internal distal support member made of Type 301 stainless steel.

Additionally, a transition zone may vary in different manners and by different degrees. Moreover, different stiffness zones can be implemented using different catheter materials, diameters, and/or thicknesses and may extend for different lengths. Thus, the stiffness profile illustrated in FIG. 5 and the materials and dimensions described are provided as one example of how embodiments can be implemented.

Moreover, a stiffness profile may include a single transition zone or multiple transition zones. The stiffness within multiple transition zones may change at the same or different rates.

Thus, the foregoing embodiments are therefore to be considered in all respects illustrative rather than limiting.

What is claimed is:

1. An intravascular steerable catheter, comprising:
an elongate flexible shaft having a proximal portion and a steerable distal portion, the distal portion of the shaft comprising:
a first section,
a second section that is proximal relative to, and stiffer than, the first section, the second section having a distal end and a proximal end, and
a third section that is proximal relative to, and stiffer than, the first section and the second section, wherein a stiffness of the second section increases gradually along its entire length from its distal end to its proximal end to gradually transition between the stiffness of the first section and the stiffness of the third section, the third section comprising:
a first segment that is proximal relative to and adjacent to the second section; and
a second segment that is proximal relative to and adjacent to the first segment, the second segment having a distal end and a proximal end, wherein the second segment of the third section is stiffer than the first segment of the third section, the first segment has a substantially constant stiffness along its length, and the stiffness of the second segment increases gradually along its entire length from its distal end to its proximal end;
wherein a rate at which the stiffness changes in the second section is less than a rate at which the stiffness changes in the second segment of the third section.

2. The catheter of claim 1, wherein the stiffness of the second section increases substantially linearly along its length between the first and third sections in a step-like or ramp-like manner.

3. The catheter of claim 1 wherein the first section has a substantially constant stiffness along its length.

4. The catheter of claim 1 wherein the first section comprises an internal support member made of a material having a yield strength greater than 120,000 psi.

5. The catheter of claim 4, wherein the support member is made of Type 301 stainless steel.

6. A steerable intravascular catheter, comprising:
a handle;
an elongate flexible shaft extending from the handle and having a proximal portion and a steerable distal portion, the distal portion of the shaft comprising a first section, a second section that is proximal relative to, and stiffer than, the first section, and a third section that is proximal relative to, and stiffer than, the first section and the second section, wherein a stiffness of the second section increases gradually along its length from a distal end to a proximal end to gradually transition between the stiffnesses of the respective first and third sections, and wherein at least one section other than the second section has a stiffness that increases gradually along at least a portion of its length, wherein a rate at which the stiffness changes in the second section is less than a rate at which the stiffness changes in the at least one section other than the second section with a gradually increasing stiffness;
an electrode carried on the steerable distal portion of the shaft; and
a wire that extends through the shaft and can be manipulated to controllably articulate the steerable distal portion in different directions.

7. The catheter of claim 6, wherein the stiffness of the second section increases substantially linearly along its length between the first and third sections in a step-like or ramp-like manner.

8. The catheter of claim 6, wherein the stiffness of at least a portion of the third section varies along its length.

9. The apparatus of claim 8, the third section comprising:
a first segment that is proximal relative to and adjacent to the second section; and
a second segment that is proximal relative to and adjacent to the first segment, wherein the second segment of the third section is stiffer than the first segment of the third section, the first segment has a substantially constant stiffness along its length, and the stiffness of the second segment increases gradually along its length from a distal end to a proximal end.

10. The apparatus of claim 9, wherein a rate at which the stiffness changes in the second section is less than a rate at which the stiffness changes in the second segment of the third section.

11. The catheter of claim 6, wherein the first section has a substantially constant stiffness along its length.

12. The catheter of claim 6, wherein the first section comprises an internal support member.

13. The catheter of claim 12, wherein the internal support member is made of a material having a yield strength greater than 120,000 psi.

14. The catheter of claim 12, wherein the internal support member is made of Type 301 stainless steel.

15. A steerable electrophysiology catheter, comprising:
a handle;
a first tubular section,
a second tubular section that is proximal relative to, and stiffer than, the first tubular section, and
a third tubular section that is proximal relative to, and stiffer than, the first tubular section and the second tubular section, wherein a stiffness of the second tubular section increases gradually along its entire length from a distal end to a proximal end to gradually transition between the stiffnesses of respective first and third tubular sections, and wherein at least one tubular section other than the second tubular section includes a stiffness that increases gradually along at least a portion of its length, wherein a rate at which the stiffness changes in the second tubular section is less than a rate at which the stiffness changes in the at least one tubular section other than the second tubular section with a gradually increasing stiffness; and
a fourth tubular section extending from the handle and being proximal relative to, and stiffer than, each of the first, second and third tubular sections;
wherein the electrophysiology catheter is a closed system from a distal end of the first tubular section to the handle.

* * * * *

UNITED STATES PATENT AND TRADEMARK OFFICE
CERTIFICATE OF CORRECTION

| | | |
|---|---|---|
| PATENT NO. | : 8,725,228 B2 | Page 1 of 1 |
| APPLICATION NO. | : 12/708114 | |
| DATED | : May 13, 2014 | |
| INVENTOR(S) | : Josef V. Koblish et al. | |

It is certified that error appears in the above-identified patent and that said Letters Patent is hereby corrected as shown below:

In the Specification

Column 1
Line 32: delete "Atria", and insert therefor --Atrial--.

Signed and Sealed this
Ninth Day of September, 2014

Michelle K. Lee
*Deputy Director of the United States Patent and Trademark Office*